United States Patent

Frigola-Constansa et al.

Patent Number: 5,182,281
Date of Patent: Jan. 26, 1993

[54] (OMEGA-(4-(2-PYRIMIDINYL)-1-PIPERAZINYL)ALKYL)-1H-AZOLE DERIVATIVES FOR THE TREATMENT OF DISORDERS OF COGNITIVE FUNCTIONS

[75] Inventors: Jordi Frigola-Constansa; Juan Pares-Corominas, both of Barcelona, Spain

[73] Assignee: Laboratorios Del Dr. Esteve, S.A., Barcelona, Spain

[21] Appl. No.: 824,995

[22] Filed: Jan. 24, 1992

[30] Foreign Application Priority Data

Jan. 25, 1991 [FR] France .................. 91 00861

[51] Int. Cl.$^5$ .................. A61K 31/50; A61K 31/495
[52] U.S. Cl. .................................. 514/252
[58] Field of Search ......................... 514/252

[56] References Cited

PUBLICATIONS

Chemical Abstracts 114:122411c (1991).
Chemical Abstracts 115:208017m (1941).

Primary Examiner—Leonard Schenkman
Attorney, Agent, or Firm—Dressler, Goldsmith, Shore, Sutker & Milnamow, Ltd.

[57] ABSTRACT

The present invention relates to the use of the derivatives of general formula I

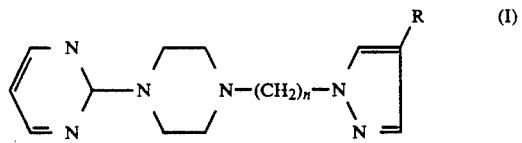

in which:

n can have values 1 to 6, and

R represents a hydrogen atom, a halogen, a $C_1$ to $C_4$ lower alkyl radical, a heteroaryl radical, a sulpho radical, an N-substituted or N,N-disubstituted sulphamoyl radical, a nitro radical, a hydroxyl radical, an oxo radical, a $C_1$ to $C_4$ lower alkoxy radical, a cyano radical, a $C_1$ to $C_4$ lower alkylcarboxylate radical, an aryl or substituted aryl radical, or an amino or substituted amino radical of formula

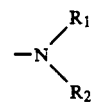

in which $R_1$ and $R_2$, which may be identical or different, represent a hydrogen atom, an alkyl radical, an aryl radical, an alkylcarbonyl radical, an arylcarbonyl radical, an alkylsulphonyl radical or an arylsulphonyl radical, the alkyl fragments of these radicals containing from 1 to 4 carbon atoms, and their therapeutically acceptable salts, for the manufacture of medicinal products intended for the treatment of disorders of cognitive funciton, such as presenile dementia, senile dementia, memory dysfunctions, deterioration of awareness and Alzheimer's disease.

2 Claims, No Drawings

(OMEGA-(4-(2-PYRIMIDINYL)-1-PIPERAZINYL-)ALKYL)-1H-AZOLE DERIVATIVES FOR THE TREATMENT OF DISORDERS OF COGNITIVE FUNCTIONS

The present invention relates to the use of {ω-[4-(2-pyrimidinyl)-1-piperazinyl]alkyl}-1H-azole derivatives, as well as their physiologically acceptable salts, for the manufacture of medicinal products intended for the treatment of disorders of cognitive function, such as presenile dementia, senile dementia, memory dysfunctions, deterioration of awareness and especially Alzheimer's disease Whereas all benzodiazepine anxiolytics have always proved incapable of treating mental disorders affecting cognitive functions, it was found, altogether surprisingly, that some {ω-[4-(2-pyrimidinyl)-1-piperazinyl]alkyl}-1H TM azole derivatives were very active for treating these particular disorders of the central nervous system.

The compounds recommended in the context of the present invention correspond to the general formula I

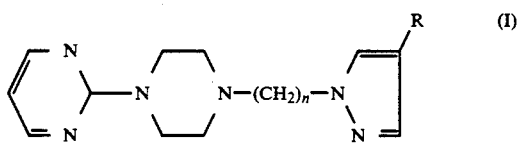

in which:
n can have values 1 to 6, and
R represents a hydrogen atom, a halogen, a C$_1$ to C$_4$ lower alkyl radical, a heteroaryl radical, a sulpho radical, an N-substituted or N,N-disubstituted sulphamoyl radical, a nitro radical, a hydroxyl radical, an oxo radical, a C$_1$ to C$_4$ lower alkoxy radical, a cyano radical, a C$_1$ to C$_4$ lower alkylcarboxylate radical, an aryl or substituted aryl radical, or an amino or substituted amino radical of formula

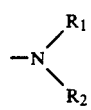

in which
R$_1$ and R$_2$, which may be identical or different, represent a hydrogen atom, an alkyl radical, an aryl radical, an alkylcarbonyl radical, an arylcarbonyl radical, an alkylsulphonyl radical or an arylsulphonyl radical, the alkyl fragments of these radicals containing from 1 to 4 carbon atoms.

These derivatives of general formula I may be prepared, in accordance with the invention, according to any one of the following methods.

Method A

By reaction of a compound of general formula II

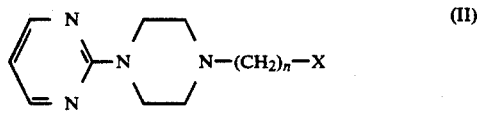

in which

X represents a halogen atom or a leaving group chosen from tosyloxy or mesyloxy, with a compound of general formula III

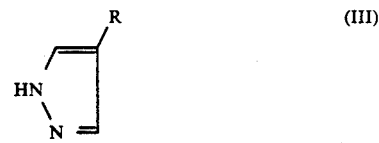

in which
R has the meanings stated above.

The reaction is performed in the presence of an appropriate solvent, for example dimethyl sulphoxide, dimethylformamide, an alcohol, a hydrocarbon, aromatic or otherwise, an ether such as dioxane or diphenyl ether, or a mixture of these solvents. This reaction is advantageously performed in the presence of a base such as alkali metal hydroxides, carbonates or bicarbonates, or alternatively a mixture of these bases. The most appropriate temperatures vary between room temperature and the refluxing temperature of the solvent, and the reaction time is between 1 hour and 24 hours.

Method B

By reduction of a compound of general formula I in which R represents a nitro group.

Among the many reducing agents capable of being used for reducing a nitro group to an amino group, the following may be mentioned: catalytic hydrogenation using nickel, palladium or platinum as catalysts, zinc amalgam with hydrochloric acid, alkali metal borohydrides, and the like.

The reaction is performed in an alcohol such as methanol, ethanol or any one of the propanols or butanols, or alternatively a mixture of an alcohol with water. The most suitable temperatures are between −10° C. and the refluxing temperature of the solvent, and the reaction time is between 1 hour and 24 hours.

Method C

By acylation of a compound of general formula I in which R represents an amino group, with an acid halide or an anhydride.

The reaction is performed without a solvent or in the presence of an appropriate solvent such as hydrocarbon, a ketone or an ether, and in the presence of a base such as pyridine or trialkylamines. The most suitable temperatures vary between −10° C. and the boiling point of the solvent, and the reaction time is between 1 hour and 24 hours.

Method D

By alkylative reduction of a compound of general formula I in which R represents a nitrogen group, this alkylative reduction being carried out with an alkali metal borohydride in the presence of nickel(II) chloride and a compound which possesses a ketone or aldehyde group. This reaction is performed in an alcohol or in a mixture of alcohol and water. The most suitable temperatures vary between −15° C. and the refluxing temperature of the solvent, and the reaction time is between a few minutes and 24 hours.

Method E

By reaction of a compound of general formula IV

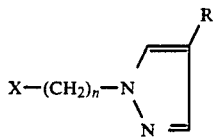

in which
X and n have the meanings stated above, with a compound of general formula V

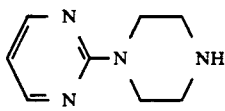

The examples which follow illustrate the preparation of a few derivatives falling within the scope of the present invention. A few modes of use will also be described.

Method A

EXAMPLE 1

Preparation of 1-{4-[4-(2-pyrimidinyl)-1-piperazinyl]butyl}-1H-pyrazole

A mixture of 4 g (13.3 mmol) of 2-(4-bromobutyl-1-piperazinyl)pyrimidine, 1.02 g (15 mmol) of pyrazole and 2.76 g (20 mmol) of potassium carbonate in 50 ml of dimethylformamide is heated to reflux for 14 hours. The mixture is evaporated under vacuum, chloroform is added, the organic phase is washed with water, dried over sodium sulphate and evaporated under vacuum and 3.5 g of an oil which is 1-(4-[4-(2-pyrimidinyl)-1-piperazinyl]butyl}-1H-pyrazole are obtained.

The compounds identified as Examples 1 to 9 are obtained by the same procedure, and the data for their identification appear in Table I.

Method B

EXAMPLE 10

Preparation of 4-amino-1-{4-[4-(2-pyrimidinyl)-1-piperazinyl]butyl}-1H-pyrazole 10.2 g (43.2 mmol) of nickel(II) chloride hexahydrate are added to a solution of 7.2 g (21 mmol) of 4-nitro-1-{4-[4-(2-pyrimidinyl)-1-piperazinyl]butyl}-1H-pyrazole, Example no. 7, in 60 ml of ethanol with vigorous stirring. The mixture is cooled in an ice bath and 10.2 g (81 mmol) of sodium borohydride are added slowly. The mixture is left stirring for 1 hour and, after 1 hour at room temperature, water is added, the mixture is evaporated under vacuum, the residue is acidified with concentrated hydrochloric acid and the resulting mixture is filtered, alkalinised with ammonia solution and extracted with ethyl ether. 4.4 g of 4-amino-1-{4-[4-(2-pyrimidinyl)-1-piperazinyl]butyl}-1H-pyrazole are thereby obtained in liquid form.

The spectroscopic data for its identification are given in Table II.

Method C

EXAMPLE 11

Preparation of 4-methylsulphonamido-1-{4-[4-(2-pyrimidinyl)-1-piperazinyl]butyl}-1H-pyrazole 1.8 g (16 mmol) of methanesulphonyl chloride are added slowly to a cooled solution of 4.4 g (14.6 mmol) of 4-amino-1-(4-[4-(2-pyrimidinyl)-1-piperazinyl]butyl}-1H-pyrazole, Example 16, in 30 ml of pyridine. The mixture is left for 1 hour at 0° C., left at room temperature for 4 hours and poured into ice-cold water, the resulting mixture is extracted with chloroform and 3.7 g of 4-methylsulphonamido-1-{4-[4-(2-pyrimidinyl)-1-piperazinyl]butyl}-1H-pyrazole are obtained, which product may be recrystallised in ethyl ether, with a melting point of 132° C.

The compounds identified a Examples 12 and 13 are obtained by the same method, and the data for their identification appear in Table II.

Method D

EXAMPLE 14

Preparation of 4-(2-butylamino)-1-{4-[4-(2-pyrimidinyl)-1-piperazinyl]butyl}-1H-pyrazole 0.9 g (24 mmol) of sodium borohydride is added to a suspension of 2.8 g (12 mmol) of nickel dichloride hexahydrate in a solution, cooled to 0° C., of 2 g (6 mmol) of 4-nitro-1-{4-[4-(2-pyrimidinyl)-1-piperazinyl]butyl}-1H-pyrazole, Example 7, and 10 ml of methyl ethyl ketone in 50 ml of ethanol. This temperature of 0° C. is maintained for 30 minutes, the mixture is allowed to rise to room temperature, stirring is continued for 2 hours, the mixture is evaporated under vacuum, the residue is taken up with ethyl acetate and 1.22 g of 4-(2-butylamino)1-{4-[4-(2-pyrimidinyl)-1-piperazinyl]-butyl}-1H-pyrazole are obtained in liquid form.

The spectroscopic data for this product are shown in Table II.

TABLE I

| Ex. | R | n | IR cm$^{-1}$ | $^1$H NMR, δ, CDCl$_3$, J=Hz |
|---|---|---|---|---|
| 1 | H | 4 | 2942, 2815, 1586, 1547, 983 | 1.50(m, 2H); 1.90(m, 2H); 2.40(m, 6H); 3.80(m, 4H); 4.12(t, 2H, J=6.9); 6.20(t, 1H, J=1.6); 6.40(t, 1H, J=4.7); 7.42(dd, 2H, J=4.7; J'=1.6); 8.25(d, 2H, J=4.7) |
| 2 | Me | 4 | 1590, 1550, 1500, 1360, 1260, 980 | 1.52(m, 2H: 1.95(m, 2H): 2.05(s, 3H): 2.37(m, 6H): 3.81(m, 4H): 4.05(t, 2H, J=6.8); 6.41)t, 1H: J=4.7)7.13 (s, 1H); 7.27(s, 1H); 7.27(s, 1H; 8.25(d, 2H, J=4.7) |
| 3 | NO$_2$ | 4 | 1584, 1524, 1480, 1444, 1406, 1359, 1305, 819 | 1.5(m, 2H): 1.93(m, 2H); 2.38(m, 6H); 3.76(m, 4H); 4.15(t, 2H, J=6.7); 6.42(t, 1H, J=4.7); 8.01(s, 1H) 8.12(s, 1H); 8.24(d, 2H, J=4.7) |
| 4 | Cl | 4 | 2843, 1586, | 1.52(m, 2H); 1.90(m, 2H); 2.43(m, 6H); 3.80(m, 4H); |

TABLE I-continued

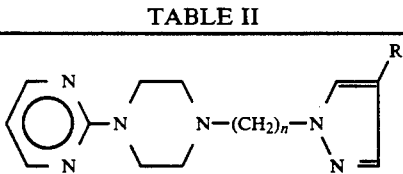

| Ex. | R | n | IR cm$^{-1}$ | $^1$H NMR, δ, CDCl$_3$, J=Hz |
|---|---|---|---|---|
|  |  |  | 1547, 1358, 983 | 4.0(t, 2H, J=6.8); 6.44(t, 1H, J=4.7); 7.35(s, 1H) 7.39 (s, 1H); 8.25(d, 2H, J=4.7) |
| 5 | Et—OOC— | 4 | 1715, 1586, 1222, 983 | 1.34(t, 3H, J=7.1); 1.54(m, 2H); 1.90(m, 2H); 2.46 (m, 6H); 3.81(m, 4H); 4.25(m, 4H); 6.47(t, 1H, J=4.7); 7.90(s, 2H); 8.29(d, 2H, J=4.7) |
| 6 | Br | 4 | 1586, 1547, 1360, 984 | 1.52(m, 2H); 1.89(m, 2H); 2.44(m, 6H); 3.62(m, 4H); 4.11(t, 2H, J=6.7); 6.46(t, 1H, J=4.6); 7.42(s, 1H); 7.45(s, 1H); 8.29(d, 2H, J=4.6) |
| 7 | C≡N | 4 | 3076, 2231, 1587, 1551, 1258, 982 | 1.54(m, 2H); 1.96(m, 2H); 2.40(m, 6H); 3.81(m, 4H); 4.20(t, 2H, J=6.9); 6.48(t, 1H, J=4.7); 7.80(s. 1H); 7.83(s, 1H); 8.29(d, 2H, J=4.7) |
| 8 | F | 4 | 2944, 1584, 1359, 1260, 1359, 1260, 983 | 1.45(m, 2H); 1.96(m, 2H); 2.36(m, 6H); 3.77(m, 4H); 4.0(t, 2H, J=6.9); 6.47(t, 1H, J=4.7); 7.27(d, 1H, J=4.8); 8.29(d, 2H, J=4.8) |
| 9 | Me—O— | 4 | 2940, 1585, 1547, 1470, 1359, 1122, 983 | 1.54(m, 2H); 1.89(m, 2H); 2.42(m, 6H); 3.77(m, 7H); 4.06(m, 2H); 6.42(t, 1H, J=4.7); 7.02(s, 1H) 7.26 (s, 1H); 8.25(d, 2J, J=4.6) |

TABLE II

| Ex. | R | M.p. | n | IR | $^1$H NMR, δ, CDCl$_3$, J=Hz |
|---|---|---|---|---|---|
| 10 | H$_2$N— | oil | 4 | 1586, 1548, 1360, 984 | 1.50(m, 2H); 1.85(m, 2H)2.43(m, 6H; 3.4(broad 2H); 3.8(m, 6H); 4.0(t, 24, J=6.4); 6.46(t, 1H, (s, 1H); 8.27(d, 2H, J=4.7) |
| 11 | Me—SO$_2$—NH— | 132° C. | 4 | 1582, 1482, 1360, 1150, 983 | 1.58(m, 2H); 1.93(m, 2H)2.45(m, 6H); 2.94(s, 3H); 3.8(m, 4H); 4.11(t, 2H, J=6.9); 6.45(t, 1H, J=4.7); 7.4(s, 1H) 7.5(s, 1H)8.28(d, 2H, J=4.7) |
| 12 | Ph—CO—NH— | 134-6° C. | 4 | 1646, 1586, 1542, 1369 | 1.55(m, 2H); 1.79(s, 3H); 1.88(m, 2H); 2.42(m, 6H); 3.80(m, 4H); 4.13(t, 2H, J=6.8); 6.51(t, 1H, J= 4.7); 7.49(m, 4H); 7.83(m, 2H); 8.0(s, 1H); 8.11 (s, 1H); 8.28(d, 2H, J=4.7) |
| 13 | Me—CO—NH— | 80-2° C. | 4 | 1650, 1586, 1454, 1364, 1261, 983 | 1.50(m, 2H); 1.88(m, 2H); 2.11(s. 3H); 2.43(m, 6H); 3.79(m, 4H); 4.08(t, 2H, J=6.8); 6.47(t, 1H, J=4.7); 7.36(s, 1H)7.93(s, 1H); 8.28(d, 2H, J=4.6); 9.25 (s, 1H) |
| 14 | Me\CH—NH—/Et | oil | 4 | 2960, 1585, 1547, 1359, 1260 983 | 1.00(t, 3H, J=7.0); 1.19(d, 3H, J-6.3); 1.6(m, 4H); 1.90(m, 2H); 2.50(m, 6H); 3.0(m, 3H); 3.9(m, 4H); 4.1(t, 2H, J=6.8); 6.52(t, 1H, J=4.7); 6.99(s, 1H); 7.17(s. 1H); 3.37(d, 2H, J=4.7) |
| 15 | Me—O—⌬— | 79-82° C. | 4 | 2390, 1589, 1545, 1495, 1360, 1247, 983, 835, 799 | 1.62(m, 2H); 1.88(m, 2H); 2.45(m, 6H); 3.81(m, 7H); 4.16(t, 2H, J=6.8); 6.46(t, 1H, J=4.7); 6.9 (d, 2H, J=4.4); 7.4(d, 2H, J=4.4); 7.55 (s, 1H); 7.7(s, 1H); 8.28(d, 2H, J=2.4) |
| 16 | Cl—⌬— | 108-110° C. | 4 | 2946, 1586, 1549, 1485, 1395, 1257, 982, 951, 830 | 1.6(m, 2H); 1.9(m, 2H); 2.46(m, 6H); 3.8(m, 4H); 4.16(t, 2H, J=6.8); 6.4(t, 1H, J=4.7); 7.36 (d, 4H, J=1.3); 7.7(d, 2H, J=6,2); 8.28 (d, 2H, J=2,3) |
| 17 | —N⟨⟩ | oil | 4 | 2943, 1586, 1487, 1359, 1260, 984, 726, | 1.55(m, 2H); 1.80(m, 2H); 2.45(m,6H); 3.81 (t, 4H, J=5); 4.12(t, 2H, J=8); 6.25 (2H, t, J=2); 6.44(1H, t, J=4.7); 6.84 (m, 2H); 7.5(d, 2H, J=5); 8.27(d, 2H, J=4.7) |

TABLE II-continued

| Ex. | (structure/R) | M.p. | n | IR cm⁻¹ | NMR |
|---|---|---|---|---|---|
| 18 | phenyl | 39–42° C. | 4 | 2942, 1585, 1493, 1446, 1359, 1258, 983, 760 | 1.6(m, 2H); 1.9(m, 2H); 2.5(m, 4H); 3.8(m, 6H); 4.2(t, 2H, J=6,8); 6.7(t, 1H, J=4.7); 7.2–7.7 (compl. abs, 5H); 8.0(s, 1H); 8.2(s, 1H); 8.4 (d, 2H, J=2.3) |
| 19 | phenyl—SO₂—NH— | 92–95° C. | 4 | 2931, 1584, 1548, 1490, 1358, 1167, 983 | 1.45(m, 2H); 1.85(m, 2H); 2.40(m, 6H); 3.80(m, 4H); 4.0(t, 2H, J=6.7); 6.47(t, 1H, J=4,6); 7.0 (s, 1H); 7.5(m, 6H); 8.3(d, 2H, J=4.6) |
| 20 | Me—phenyl—SO₂—NH | 108–110° C. | 4 | 2943, 1585, 1548, 1446, 1360, 1161, 984 | 1.5(m, 2H); 1.85(m, H); 2.28(m, 9H); 3.8(m, 4H); 4.0(m, 2H); 6.45(t, 1H, J=4,7); 7–7.65 (m, 6H); 8.27(d, 2H, J=4.7) |
| 21 | n-Bu—SO₂—NH— | oil | 4 | 2941, 1586, 1548, 1448, 1360, 1146, 984, 755 | 0.91(t, 3H, J=6,8); 1.45(m, 4H); 1.85(m, 4H); 2.40(m, 6H); 3.0(m, 2H); 3.80(m, 4H); 4.11 (t, 2H, J=6.5); 6.5(t, 1H, J=4.7); 7.4 (m, 2H); 7.5(s, 1H); 8.3(d, 2H, J=4.7) |
| 22 | n-Pr—SO₂—NH— | oil | 4 | 2940, 1586, 1548, 1447, 1360, 1146, 984, 755 | 1.0(t, 3H, J=7.1); 1.55(m, 2H); 1.9(m, 4H); 2.45(m, 6H); 3.0(t, 2H, J=7.4); 3.8 (m, 4H); 4.1(t, 2H, J=6.4); 6.46 (t, 1H, J=4.7); 7.35(m, 2H); 7.55(s, 1H); 8.3 (d, 2H, J=4.7) |
| 23 | Et—SO₂—NH— | Huile | 4 | 2943, 1586, 1548, 1447, 1360, 1146, 984, 754 | 1.36(m, 5H); 1.9(m, 2H); 2.45(m, 6H); 3.0(m, 2H); 3.6(m, 4H); 4.1(t, 2H, J=6,4); 6.45 (t, 1H, J=4.7); 7.39(s, 1H); 7.51(s, 1H); 8.3(d, 2H, J=4.7) |
| 24 | —SO₂—N—Me₂ | 100–102° C. | 4 | 3135, 2943, 1586, 1512, 1357, 1328, 1156, 982, 728 | 1.6(m, 2H); 1.9(m, 2H); 2.3–2.7(conc. abs. 13H); 3.8(m, 4H); 4.2(t, 2H, J=6.8); 6.4 (t, 1H, J=4.7); 7.75(d, 1H, J=4.4); 8.28 (d, 2H, J=2.4) |
| 25 | —SO₃—H | 230–235° C. (dec.) | 4 | 3330, 1590, 1556, 1449, 1220, 1178, 1049, 971, 656 | 1.95(m, 2H); 3.3(m, 6H); 4.0(s, 5H); 4.27 (t, 2H, J=6.1); 6.8(t, 1H, J=4.8); 7.8 (s, 1H); 8.0(s, 1H); 8.43(d, 2H, J=2.4) |

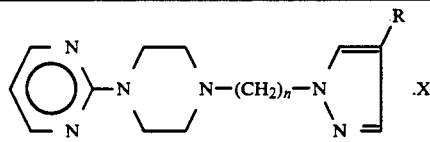

| Ex. | R | X | M.p. | n | IR cm⁻¹ |
|---|---|---|---|---|---|
| 26 | Cl | 1 HCl | 156–158° C. | 4 | 3490, 1592, 1556, 1481, 1438, 1386, 970 |
| 27 | Cl | 2 HCl.H₂O | 194–197.5° C. | 4 | 3429, 2688, 1636, 1620, 1346, 1218, 971 |

ACTIVITY FOR THE IMPROVEMENT OF COGNITION

The existence of activity for the improvement cognition is demonstrated for the compounds of the above-mentioned formula I in the following manner:

The influence of the test products on the process of habituation of mice is studied in the light/dark box test described by J. M. Barnes et al. (Pharmacol. Biochem. Behav., 1990, 33, 955–962). On the one hand the effect on learning (the speed of habituation) and on the other hand the capacity for blockade of the contrary effects produced by scopolamine, are studied.

The mouse is placed in the light area of a box divided into two compartments, one brightly lit, the light box, and the other poorly lit, the dark box.

(1) The number of times the mouse rears on its hind legs in each compartment is counted during 5 minutes (see column 1 of the table below).

(2) The activity in each compartment is given by a count of the number of crossings over the squares which make up the divisions of each compartment (see column 2 of the table below).

(3) The time spent in the dark box is measured during the 5 minutes of the count (see column 3 of the table below).

(4) The initial latency, that is to say the time elapsing between placing the animal in the light box at the beginning of the trial and its entry into the dark box, is determined (see column 4 of the table below).

The control animals are administered two treatments per day using the excipient alone. The animals treated with the compound under study are administered ip two doses per day of 0.01 mg/kg of this product. The same operation is repeated daily during 3 days. The animals learn to remain in the dark box for a longer time and to go there more rapidly.

On the fourth day, scopolamine (2 × 0.25 mg/kg, ip) is administered. With this treatment, the animals of the control group "forget" the learned behaviour which consists in remaining in the dark box for a longer time.

Treatment with a product which improves cognition results in:

(1) the learned behaviour being improved, learning taking place more rapidly and the residence time in the dark box increasing.
(2) the scopolamine-induced reversal of learning being completely blocked.

The data obtained are summarised in Table III. They demonstrate, on the basis of the results obtained, for example, with the compound of Example 27, an activity of improvement of cognition, since this compound improves the learning process and blocks the effects of scopolamine. Piracetam tested under the same conditions has no activity.

In human therapy, the dose administered is naturally dependent on the severity of the particular disorders of the central nervous system.

It will generally be between approximately 5 and approximately 100 mg/day.

The derivatives of the invention will, for example, be administered in the form of tablets, solutions or suspensions, or alternatively of gelatin capsules.

As examples, two particular pharmaceutical dosage forms appear below.

TABLE III

INFLUENCE OF THE COMPOUND OF EXAMPLE 27 (0.01 MG/KG, IP, TWICE PER DAY) ON THE PROCESS OF HABITUATION IN MICE DETERMINED BY THE LIGHT/DARK BOX TEST.

| DAY OF TREATMENT | REARING POSTURES IN 5 MIN. | | ACTIVITY IN 5 MIN | | TIME IN BOX | | LATENCY | |
|---|---|---|---|---|---|---|---|---|
| | CONTROL L - D | EXAMPLE 27 L - D | CONTROL L - D | EXAMPLE 27 L - D | CONTROL D | EXAMPLE 27 D | CONTROL L - D | EXAMPLE 27 L - D |
| 1 | 22  70 | 22  78 | 35  82 | 38  85 | 59 | 60 | 9 | 9 |
| 2 | 23  71 | 8  125 * * | 36  83 | 12  138 * * | 60 | 87 * | 7 | 2 * |
| 3 | 19  72 | 8  130 * * | 30  84 | 8  145 * * | 60 | 80 | 7 | 0.5 * |
| 4(*) | 40  20 + + | 7  125 * * o  o | 55  30 + + | 9  148 * * o  o | 20 + | 80 * o | 24 + | 1 * o |

(*) 2 prior treatments with scopolamine (0.25 mg/kg, ip)
* p < 0.001 (improvement in learning compared with day 1)
+ p < 0.001 (reversal of the process of habituation produced by scopolamine)
o p < 0.001 (inhibition of the effect of scopolamine)
L - D: light - dark

ANTIDEPRESSANT ACTIVITY

In addition, the existence of antidepressant activity was demonstrated for Example 27 using the hopeless behaviour test in mice described by R. D. Porsolt et al. (Arch. Int. Pharmacodyn., 1977, 229, 327-336). The animals are placed for 6 minutes in a cylinder containing water from which they cannot escape. The period of immobility between minutes 2 and 5 is measured in groups of 10 mice per dose tested.

The product under study is administered ip 1 hour before the test. In this test, the immobility of the animals is explained as a product of their depressive ("hopeless") state as a consequence of being faced with an adverse and insoluble situation in a hostile environment like water. Antidepressants reduce this immobility. In our trial, imipramine (30 mg/kg, ip) was used as a reference product.

The results demonstrate that the compound 27 has antidepressant activity, since it significantly reduces the period of immobility of the control group.

| Product | Dose (mg/kg, ip) | Period of immobility (seconds) |
|---|---|---|
| Control | — | 87 |
| Example 27 | 1 | 58 (p 0.005) |
| Imipramine | 30 | 32 (p 0.005) |

The derivatives of general formula I according to the invention are hence useful as active substances of medicinal products intended for the treatment of disorders associated with cognition, such as senile dementia, memory dysfunctions, deterioration of awareness, and the like, as well as depressive states.

| Example of formula per tablet | |
|---|---|
| Compound 27 | 5 mg |
| Lactose | 60 mg |
| Microcrystalline cellulose | 25 mg |
| Povidone | 5 mg |
| Pregelatinised starch | 3 mg |
| Colloidal silica | 1 mg |
| Magnesium stearate | 1 mg |
| Tablet weight | 100 mg |

| Example of formula per gelatin capsule | |
|---|---|
| Compound 27 | 10 mg |
| Polyoxyethylenated glycerol | 135 mg |
| Glyceryl behenate | 5 mg |
| | 150 mg |
| Excipient: soft gelatin q.s. | |

We claim:

1. Process of treating a patient suffering from loss of cognitive function which comprises administering to said patient an effective amount of at least one compound of formula I

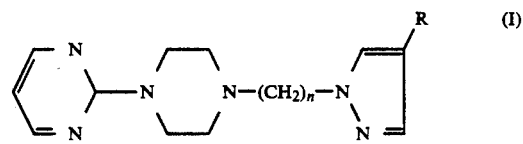

in which:
n can have values 1 to 6, and
R represents a hydrogen atom, a halogen, a $C_1$ to $C_4$ lower alkyl radical, a heteroaryl radical, a sulpho radical, an N-substituted or N,N-disubstituted sulphamoyl radical, a nitro radical, a hydroxyl radical, an oxo radical, a $C_1$ to $C_4$ lower alkoxy radical, a cyano radical, a $C_1$ to $C_4$ lower alkylcarboxylate radical, an aryl or substituted aryl radical, or an amino or substituted amino radical of formula

in which

R₁ and R₂, which may be identical or different, represent a hydrogen atom, an alkyl radical, an aryl radical, an alkylcarbonyl radical, an arylcarbonyl radical, an alkylsulphonyl radical or an arylsulphonyl radical, the alkyl fragments of these radicals containing from 1 to 4 carbon atoms, and the therapeutically acceptable salts of such compounds.

2. Process according to claim 1, characterised in that the compound of formula I is chosen from:

1—1-{4-[4-(2-pyrimidinyl)-1-piperazinyl]butyl}-1H-pyrazole,
2—4-methyl-1-{4-[4-(2-pyrimidinyl)-1-piperazinyl]butyl}-1H-pyrazole,
3—4-nitro-1-{4-[4-(2-pyrimidinyl)-1-piperazinyl]butyl}-1H-pyrazole,
4—4-chloro-1-{4-[4-(2-pyrimidinyl)-1-piperazinyl]butyl}-1H-pyrazole,
5—4-ethoxycarbonyl-1-{4-[4-(2-pyrimidinyl)-1-piperazinyl]butyl}-1H-pyrazole,
6—4-bromo-1-{4-[4-(2-pyrimidinyl)-1-piperazinyl]butyl}-1H-pyrazole,
7—4-cyano-1-{4-[4-(2-pyrimidinyl)-1-piperazinyl]butyl}-1H-pyrazole,
8—4-fluoro-1-{4-[4-(2-pyrimidinyl)-1-piperazinyl]butyl}-1H-pyrazole,
9—4-methoxy-1-{4-[4-(2-pyrimidinyl)-1-piperazinyl]butyl}-1H-pyrazole,
10—4-amino-1-{4-[4-(2-pyrimidinyl)-1-piperazinyl]butyl}-1H-pyrazole,
11—4-methylsulphonamide-1-{4-[4-(2-pyrimidinyl)-1-piperazinyl]butyl}-1H-pyrazole,
12—4-benzamido-1-{4-[4-(2-pyrimidinyl)-1-piperazinyl]-butyl}-1H-pyrazole,
13—4-acetamido-1-{4-[4-(2-pyrimidinyl)-1-piperazinyl]butyl}-1H-pyrazole,
14—4-(2-butylamino)-1-{4-[4-(2-pyrimidinyl)-1-piperazinyl]butyl}-1H-pyrazole,
15—4-(4-methoxyphenyl)-1-{4-[4-(2-pyrimidinyl)-1-piperazinyl]butyl}-1H-pyrazole,
16—4-(4-chlorophenyl)-1-{4-[4-(2-pyrimidinyl)-1-piperazinyl]butyl}-1-H-pyrazole,
17—4-(1-pyrrolyl)-1-{4-[4-(2-pyrimidinyl)-1-piperazinyl]butyl}-1H-pyrazole,
18—4-phenyl-1-{4-[4-(2-pyrimidinyl)-1-piperazinyl]butyl}-1H-pyrazole,
19—4-phenylsulphonamido-1-{4-[4-(2-pyrimidinyl)-1-piperazinyl]-butyl}-1H-pyrazole,
20—4-(4-methylphenylsulphonamido)-1-(4-[4-(2-pyrimidinyl) -1-piperazinyl]butyl}-1H-pyrazole,
21—4-butylsulphonamido-1-{4-[4-(2-pyrimidinyl)-1-piperazinyl]butyl}-1H-pyrazole,
22—4-propylsulphonamido-1-{4-[4-(2-pyrimidinyl)-1-piperazinyl]butyl}-1H-pyrazole,
23—4-ethylsulphonamido-1-{4-[4-(2-pyrimidinyl)-1-piperazinyl]butyl}-1H-pyrazole,
24—4-(N,N-dimethylsulphamoyl)-1-{4-[4-(2-pyrimidinyl) -1-piperazinyl]butyl}-1H-pyrazole,
25—4-sulpho-1-{4-[4-(2-pyrimidinyl)-1-piperazinyl]butyl}-1H-pyrazole,
26—4-chloro-1-{4-[4-(2-pyrimidinyl)-1-piperazinyl]butyl}-1H-pyrazole hydrochloride,
27—4-chloro-1-{4-[4-(2-pyrimidinyl)-1-piperazinyl]butyl}-1H-pyrazole dihydrochloride.

* * * * *

UNITED STATES PATENT AND TRADEMARK OFFICE
CERTIFICATE OF CORRECTION

PATENT NO. : 5,182,281
DATED : January 26, 1993
INVENTOR(S) : Jordi Frigola-Constansa and Juan Pares-Corominas It is certified that error appears in the above-identified patent and that said Letters Patent is hereby corrected as shown below:

In the Abstract, in column 1, line 25, and in claim 1, Formula (I), there should be a second bond shown in the left six-membered ring between the nitrogen atom in the upper right portion of the ring and the carbon atom to which the remainder of the structure is joined.

Column 5, Table I, Experiment 8, 4th column, line 2, "1359, 1260" should be --1546, 1507--;
    Experiment 9, 5th column, last line, "(d,2J,J=4.6)" should be --(d,2H,J=4.6)--;
    Table II, Experiment 10, 6th column, line 3, before "(S,1H)" insert --J=4.7);6.98(s,1H);7.10--;
    Experiment 17, 6th column line 2, "J=8" should be --J=7--.

Column 7, Table II, Experiment 22, 6th column, line 4, "7.55" should be --7.5--.

Signed and Sealed this

Fourth Day of January, 1994

*Attest:*

BRUCE LEHMAN

*Attesting Officer*     Commissioner of Patents and Trademarks